(12) United States Patent
Dirkes

(10) Patent No.: US 9,924,914 B2
(45) Date of Patent: Mar. 27, 2018

(54) X-RAY RECORDING SYSTEM

(71) Applicant: SIEMENS AKTIENGESELLSCHAFT, Munich (DE)

(72) Inventor: Guido Heinrich Dirkes, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 197 days.

(21) Appl. No.: 15/003,842

(22) Filed: Jan. 22, 2016

(65) Prior Publication Data

US 2016/0213329 A1    Jul. 28, 2016

(30) Foreign Application Priority Data

Jan. 22, 2015   (DE) .................. 10 2015 201 070

(51) Int. Cl.
*A61B 6/00*   (2006.01)
*A61B 6/08*   (2006.01)

(52) U.S. Cl.
CPC .............. *A61B 6/4452* (2013.01); *A61B 6/08* (2013.01); *A61B 6/545* (2013.01); *A61B 6/4441* (2013.01);
(Continued)

(58) Field of Classification Search
CPC ......... A61B 6/08; A61B 6/545; A61B 6/0457; A61B 6/542; A61B 6/547
See application file for complete search history.

(56) References Cited

U.S. PATENT DOCUMENTS 4,894,855 A * 1/1990 Kresse .................. A61B 6/032
                                                378/189
2002/0118793 A1 * 8/2002 Horbaschek ......... A61B 6/4233
                                                378/197
(Continued)

FOREIGN PATENT DOCUMENTS

CN      103735268 A      4/2014
EP      2954843 A1 * 12/2015  ............... A61B 6/08
(Continued)

OTHER PUBLICATIONS

Kinect, Wikipedia—Kinect. From the Wayback Machine by Internet Archive. Retrieved from the Internet: <URL:https://web.archive.org/web/20140120153555/https://en.wikipedia.org/wiki/Kinect>. Published on Jan. 20, 2014.*

*Primary Examiner* — Glen Kao
(74) *Attorney, Agent, or Firm* — Laurence Greenberg; Werner Stemer; Ralph Locher

(57) ABSTRACT

An x-ray recording system contains an x-ray emitter for generating a beam used for imaging, an imaging x-ray detector with a two-dimensional or three-dimensional recording geometry for determining the attenuation of the rays of the beam, a patient bearing and/or positioning device for a patient in a recording region of the x-ray recording system between the x-ray emitter and the x-ray detector. A time of flight (TOF) camera is arranged for establishing the contour of the patient and a computer with a memory and software stored therein is present, which computer unit is embodied, during operation, to generate a three-dimensional wire model of the patient with joint locations arranged therein from the contour of the patient recorded by the TOF camera and to simulate and display at least one anatomical structure scaled to the wire model.

12 Claims, 3 Drawing Sheets

(52) U.S. Cl.
CPC ........... *A61B 6/4464* (2013.01); *A61B 6/4476* (2013.01); *A61B 6/462* (2013.01); *A61B 6/466* (2013.01); *A61B 6/587* (2013.01)

(56) References Cited

U.S. PATENT DOCUMENTS

| | | | |
|---|---|---|---|
| 2011/0102549 | A1 | 5/2011 | Takahashi |
| 2013/0342350 | A1* | 12/2013 | Popescu ................ G08B 21/02 340/573.1 |
| 2014/0348296 | A1 | 11/2014 | Goossen et al. |
| 2015/0092998 | A1 | 4/2015 | Liu et al. |
| 2017/0119338 | A1* | 5/2017 | Merckx ................ A61B 6/545 |

FOREIGN PATENT DOCUMENTS

| | | | |
|---|---|---|---|
| KR | 20100139049 | A | 12/2010 |
| KR | 20120103143 | A | 9/2012 |
| KR | 20130095663 | A | 8/2013 |
| KR | 20150006288 | A | 1/2015 |
| WO | 2013072872 | A1 | 5/2013 |

* cited by examiner

X-RAY RECORDING SYSTEM

CROSS-REFERENCE TO RELATED APPLICATION

This application claims the priority, under 35 U.S.C. § 119, of German application DE 10 2015 201 070.8, filed Jan. 22, 2015; the prior application is herewith incorporated by reference in its entirety.

BACKGROUND OF THE INVENTION

Field of the Invention

The invention relates to an x-ray recording system containing at least an x-ray emitter for generating a beam used for imaging, an imaging x-ray detector with a two-dimensional or three-dimensional recording geometry for determining the attenuation of the rays of the beam, and a patient bearing device for bearing a patient in a recording region of the x-ray recording system between the x-ray emitter and the x-ray detector.

X-ray recording systems of the aforementioned type are well known. In such x-ray recording systems, patients are generally arranged on a couch by medical assistants, or else by a medical practitioner, and the body part to be irradiated is visually positioned relative to the x-ray tube and x-ray detector with the aid of light fields, which depict or delimit the recording region, in accordance with the medical question. On the one hand, if the alignment of the recording region is too tight such that part of the region to be recorded was not imaged in the x-ray image, another recording with the consequence of more exposure to radiation is required. On the other hand, if the recording region is dimensioned to be too large so as to avoid the aforementioned problem, there is unnecessary exposure to radiation in the edge regions. A further problem also emerges from the alignment of the beam axis of the x-ray emitter, which needs to be selected correctly. If an incorrect projection direction is selected in this case, it may be that structures or organs to be displayed are covered or superposed by other structures or organs such that, in turn, another recording from a different projection angle becomes necessary in order to obtain a medically relevant x-ray image.

SUMMARY OF THE INVENTION

It is therefore an object of the invention to find an x-ray recording system which enables more reliable positioning of the recording field and more reliable alignment of the x-ray beam axis.

The inventor has identified that, for an x-ray recording, it is possible to achieve a substantially higher reliability in respect of the correct positioning of the recording region and the correct alignment of the beam direction of the x-ray emitter in relation to the x-ray detector if this aligning is carried out by a simulated display of anatomical structures on the patient or by a superposition of the structures with an image of the patient.

This can be realized by the use of a time of flight (TOF) camera, for example by assembling a Kinect sensor from Microsoft or an XTION sensor from ASUS on the x-ray tube, in particular at the x-ray head or in the vicinity of the x-ray detector. Particularly in the case of sub-table systems, it is possible to acquire the location and position of the patient very well in the form of a three-dimensional wire model, with it then being possible to image the anatomical structures of the patient in a scaled manner in accordance with the patient contour. By identifying the joint locations and optionally also the endpoints of the extremities and of the body, it is possible to acquire, in particular, the bone structures present in a very exact manner and depict these in a simulated fashion as an image. In principle, such a simulation of bone structures is known from "skeleton tracking", as is used in games consoles. Transferred onto an x-ray system and improved by an anatomically exact display of the skeleton and optionally complemented with the scaled organ positions or simulated organ contours, what emerges is a superposition of the expected anatomical structures, in particular the bone structures, which is optimized to the individual patient and scaled in a fitting manner. This can optionally take place on a conventional monitor or as a projection directly onto the patient. As a result of this, it is then possible to set the desired recording region in a substantially more exact manner than when carried out by the ultimately intuitive actions of medical staff.

Additionally, the position acquisition renders it possible for the beam axis to be adapted to the current position of the anatomical structures. This provides a substantial easing of the workload for the operator, particularly in the case of x-ray systems with many degrees of freedom in respect of the spatial alignment of the x-ray emitter and of the x-ray detector, such as in the case of e.g. the YSIO radiography system from the applicant.

The complete beam geometry of the x-ray recording system can be aligned with the position of the patient in an automated manner for the respective medical question by way of such an identification system of anatomical structures.

In accordance with this discovery, the inventor proposes an x-ray recording system which contains at least an x-ray emitter for generating a beam used for imaging, an imaging x-ray detector with a two-dimensional or three-dimensional recording geometry for determining the attenuation of the rays of the beam, and a patient bearing and/or positioning device in a recording region of the x-ray recording system between the x-ray emitter and the x-ray detector. According to the invention, at least one TOF camera is arranged—preferably above the patient couch—for establishing the contour of the patient and a computer unit with a memory and software stored therein is to be present. The computer unit is embodied, during operation, to generate a three-dimensional wire model with joint locations arranged therein from the contour of the patient recorded by the TOF camera and to simulate and display at least one anatomical structure scaled to the wire model.

Due to the better placement and alignment of the x-ray recordings across the board, improved beam hygiene therefore emerges as non-relevant regions of the patient are no longer unnecessarily exposed to radiation and images with a greater diagnostic value are created as the beam geometry is optimized in relation to the diagnostic question. Furthermore, there is also an increase in comfort for the patient in modalities with many spatial degrees of freedom since the beam field can in this case be adapted to the position of the patient or of the anatomical structure to be examined.

Advantageously, a skeleton or bony skeleton, a venous or arterial structure or an organ structure can, in particular, be simulated as an anatomical structure and displayed. It is particularly advantageous—particularly in relation to such a display of organ locations and contours—if standardizing parameters of the patient in this respect, such as e.g. sex, age, height and weight, are additionally entered in advance, which parameters are considered in the simulated placement of the organs. To this end, it is possible to carry out a corresponding statistical examination in advance on the basis of available CT and/or MRI data in order to determine the relevance of the respective parameters and the effect thereof on the positioning of the organs.

Furthermore, it is advantageous if a projection system is present, which projects the at least one anatomical structure onto the patient situated on the patient bearing device. As a result, the position of the anatomical structures is directly shown to the operating staff on the patient, and so manual setting of the beam geometry of the x-ray recording system is made possible without problems. This also applies, in particular, in radiography systems in which the emitter and the detector can be positioned independently of one another. In this case, it should also be mentioned that, in combination with the invention described here, it is also possible to image the respectively present x-ray recording field on the patient by correspondingly variable light frames.

It is also advantageous if the software stored in the computer unit is additionally embodied to set the patient positioning in an automated manner in accordance with the at least one anatomical structure on the basis of a predetermined recording region by setting the patient bearing and/or positioning device and/or setting location and position of the x-ray emitter and/or x-ray detector relative to one another and to the patient.

What is furthermore proposed is that a normal optical camera which depicts the patient on a monitor is also present, wherein the software stored in the computer unit is also embodied to superpose, on the monitor, the simulated anatomical structure with a representation of the patient. If the normal optical camera is a 3D camera permitting 3D representations, the superposition of the optical recording and the simulated anatomical structure in the patient can also be carried out in 3D. Additionally, it is also possible, particularly if 3D representations are present, to depict the positioning of the x-ray recording system, possibly including the beam, on the monitor.

If an automatic alignment of the beam geometry relative to the patient is used within the scope of the invention, the recording situation and beam geometry, which was set automatically, can be re-checked by the staff prior to the actual x-ray recording and corrected by the operating staff where necessary.

It is also expedient if the software stored in the computer unit is embodied to automatically align the spatial position of the x-ray emitter in accordance with anatomical structures to be recorded. In the process, a table or database can be stored, which specifies the ideal alignment of the x-ray emitter relative to a predetermined structure.

What is proposed in a particular embodiment variant of the x-ray recording system is that the TOF camera is part of a KINECT or XTION acquisition system. As a result of this, it is possible to resort to very economical system components, for which it is also possible to use already available SDKs (software development kits) for programming purposes, and so the development of the software can be carried out in an economical manner.

In principle, the TOF camera should be arranged next to the x-ray emitter or next to the x-ray detector, with respectively that side from which it is possible to observe the patient without an obstacle lying there-between being selected.

In particular, the x-ray recording system can be configured as a C-arm system or as a projective radiography system. Here, the radiography system can also be embodied in such a way that the x-ray emitter and the x-ray detector are arranged on articulated arms in a manner independent of one another and freely movable in space. The Ysio radiography system from the applicant provides an example of this.

Other features which are considered as characteristic for the invention are set forth in the appended claims.

Although the invention is illustrated and described herein as embodied in a x-ray recording system, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Below, the invention will be described in more detail on the basis of the figures, with only the features required for understanding the invention being depicted. The following reference signs are used in the figures: 1: TOF camera; 2: x-ray tube; 2.1: telescope and articulation system; 3: x-ray detector/flat-panel detector; 3.1: telescope and articulation system; 4: rail system; 6: housing; 7: C-arm; 8: patient couch; 9: computer unit; G: wire model; O: organ system; P: patient; S: skeleton/bony skeleton; V: venous and arterial system; Prg1-Prgn: software/programs.

Figure 1:
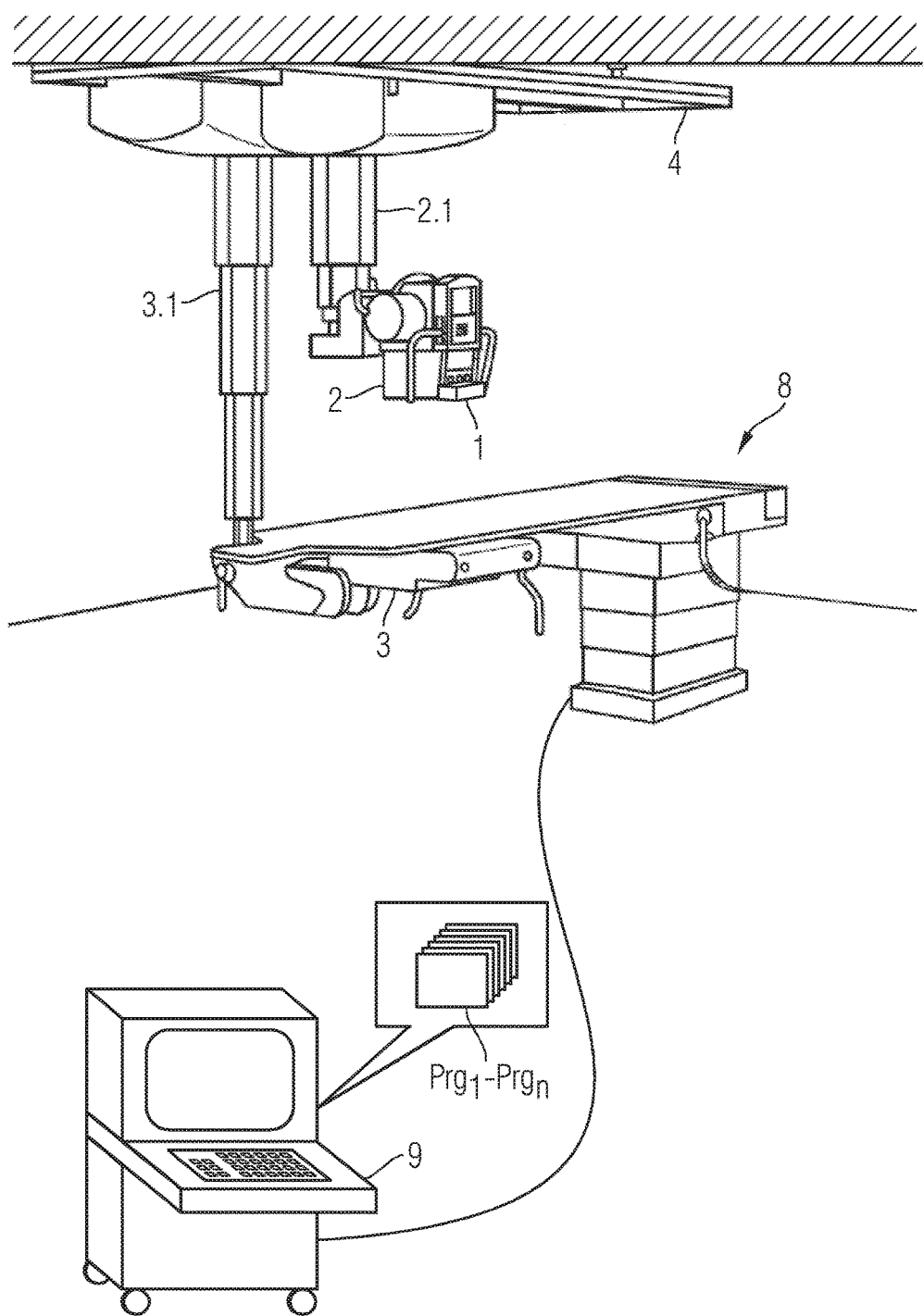
FIG. 1 is a diagrammatic, perspective view of a radiography system according to the invention for generating projective x-ray recordings, with a TOF camera.

Referring now to the figures of the drawings in detail and first, particularly to FIG. 1 thereof, there is shown an exemplary radiography system according to the invention, by which projective x-ray recordings of patients can be generated. Such a radiography system contains a patient positioning system, in this case in the form of a patient couch or table 8, which is embodied in a manner adjustable both in terms of the height thereof and in terms of at least one horizontal direction. If the patient is born on the patient couch, it is possible to set both an x-ray tube 2 and a digital flat-panel detector 3 to have any spatial locations and any alignments with the aid of a telescope and articulation systems 2.1 and 3.1 thereof. In the present example, both telescope and articulation systems 2.1 and 3.1 are connected in a horizontally displaceable manner to a ceiling of the room by way of a rail system 4.

What should be observed in each case for an x-ray recording is that a coordinated alignment between the x-ray tube 2 and the flat-panel detector 3 is brought about in such a way that, first, in respect of the desired active recording region thereof, the detector 3 is covered by the x-ray radiation and, second, the x-ray radiation should where possible not extend beyond the recording region such that there is no unnecessary exposure of the patient to radiation. Moreover, the alignment of the x-ray radiation and the recording region of the detector 3 must be set in such a way that as few perspective distortions as possible are created. This already is not a trivial problem for the operating staff, particularly in the case of x-ray tubes and detectors that are freely movable relative to one another.

Finally, in order to avoid unnecessary exposure to radiation, it is also necessary to set the x-ray radiation as exactly as possible onto the recording region on the patient that is required for making findings, for example for recording a specific region of the skeleton, a predetermined organ or an organ system containing a plurality of organs. To this end, the operating staff requires well-founded anatomical knowledge. However, despite intensive training, there are repeated occurrences where the undertaken settings are insufficient and hence regions that are too large are irradiated unnecessarily or it is necessary to carry out correction recordings as the first recording did not completely cover the desired region.

Therefore, according to the invention, use is made of a time-of-flight camera 1 and the patient P is scanned in respect of his contours using the TOF camera 1, which in this case is assembled on the x-ray tube 2. From knowledge about the contour of the patient, it is then possible to calculate a wire model of the skeleton with typical joint locations. Corresponding computer programs for generating such a wire model—registered/adapted to the contour of the patient—are well known and also made freely available by the manufacturers of the TOF cameras as software development kit (SDK).

If the wire model with its typical joint locations and distances between the joint locations is available, it is possible to register a previously established general model of anatomical structures on the established wire model such that a display of anatomical structures adapted to the proportions of the patient is made possible and the structures in turn can be projected directly onto the patient with the aid of a projector, or it is possible to superpose onto an image recording of the patient the established virtual anatomical structure on a monitor.

In the present example, such an image projector should be integrated directly into the housing of the TOF camera 1. The above-described establishment of the wire model and also the adaptation of the virtual anatomical structures can take place on the computer system 9 with the aid of the programs Prg1-Prgn that are stored therein and executed during operation. Instead of projecting the organic structures onto the patient, it is possible to display a superposition of the virtual structures and an optical recording of the patient on the monitor of the computer system.

If the operating staff now has the anatomical structure of the patient to be examined optically in view relative to said patient, it is possible to control the alignment of x-ray tube 2 and detector 3 substantially more exactly than previously.

Additionally, reference is made to the fact that the way that the patient is borne shown here is merely intended to be exemplary. By way of example, the bearing aids according to the invention can also be used for instances of patient positioning in which the patient is imaged in a standing position for a recording of the lungs or in which the patient is examined in a seated position.

Figure 2:
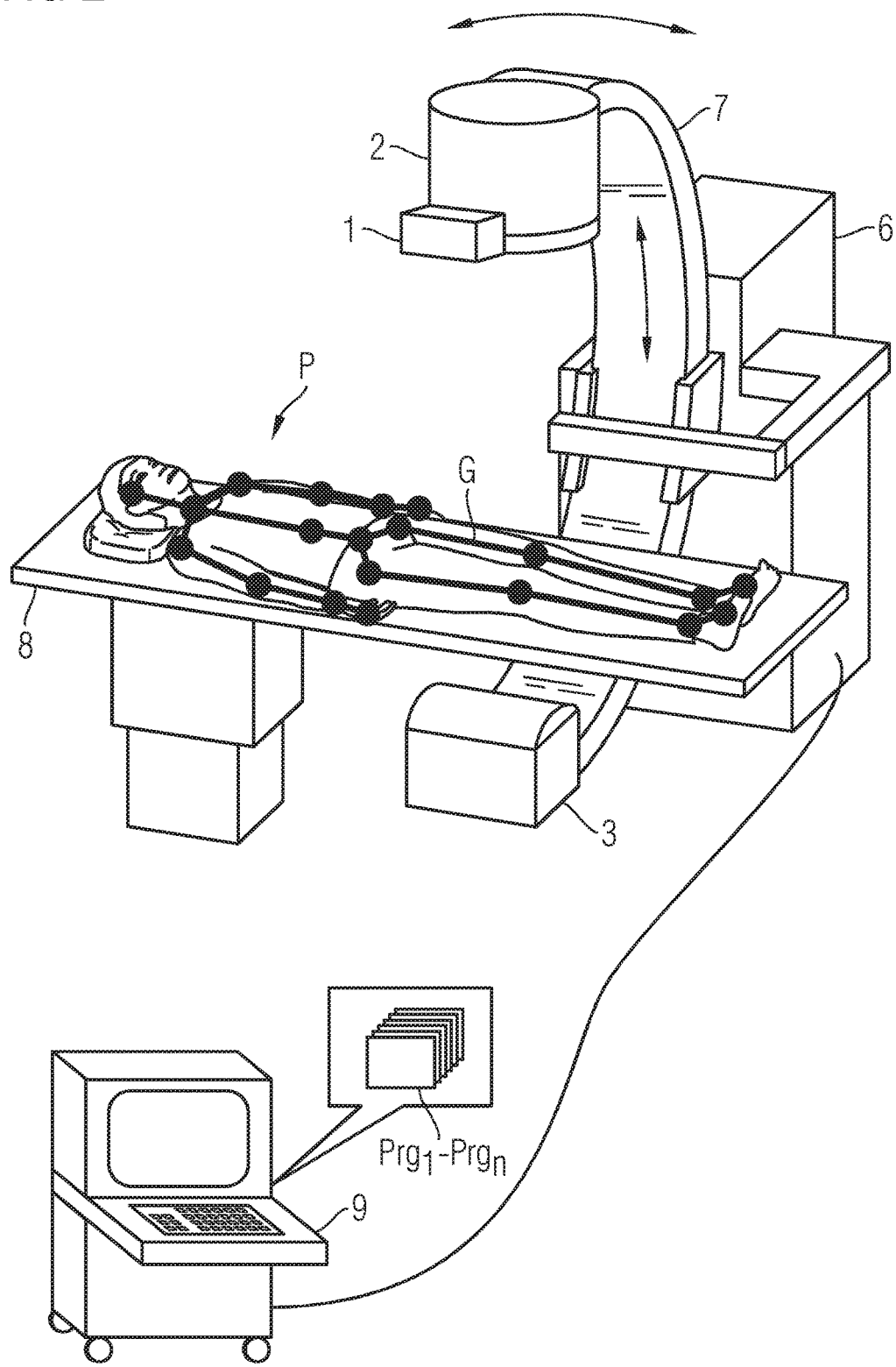
FIG. 2 is a diagrammatic, perspective view of a C-arm system according to the invention with the TOF camera.

The embodiment of an x-ray system according to the invention can also be brought about in conjunction with a C-arm system, as shown in FIG. 2 in an exemplary manner. This C-arm system typically likewise contains an x-ray tube 2 and a digital flat-panel detector 3, wherein, however, these two units are securely connected and aligned relative to one another by way of a swivelable and rotatable C-arm 7. The C-arm 7 is moved by an appropriate mechanism, which is situated in the housing 6 and the control of which is carried out by the computer system 9 with the aid of appropriate programs Prg1-Prgn.

In the shown embodiment, the TOF camera 1 is once again fastened to the x-ray tube 2. In order to elucidate the invention, a wire model G is also shown on the patient P, which wire model is created according to the invention with the aid of the TOF camera 1 and appropriate software in the computer system 9 and which wire model is adapted to the proportions of the patient currently situated on the patient couch 8.

Figure 3:
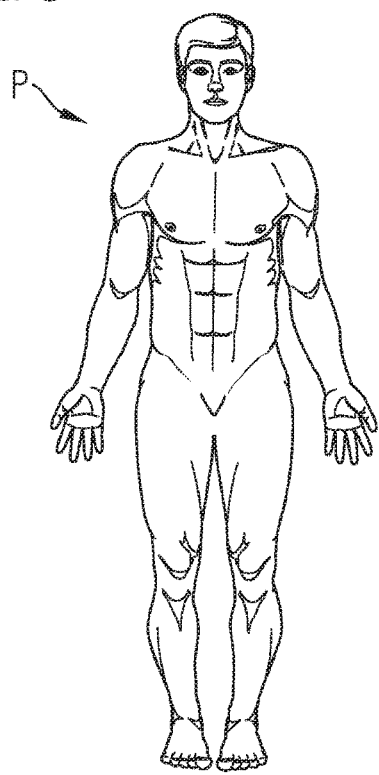
FIG. 3 is an illustration of a patient.
Figure 4:
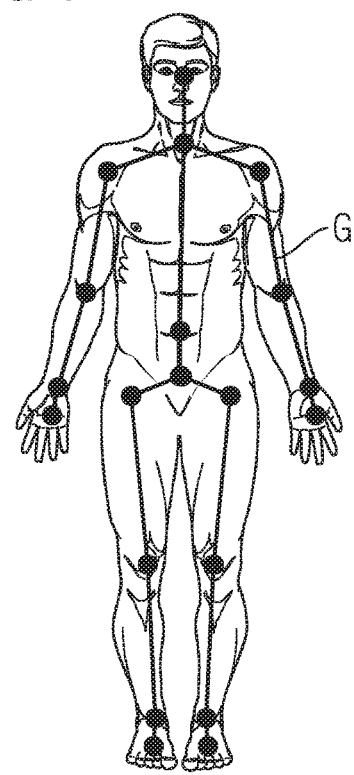
FIG. 4 is an illustration of a wire model registered on the patient.

FIGS. 3 to 7 once again elucidate the procedure according to the invention for assisting a correct alignment of x-ray recordings in the case of a projective x-ray system. FIG. 3 shows the contours of a patient P on a patient couch, as are recorded by a TOF camera. By applying appropriate, currently freely available SDKs, it is possible to create a wire model G of the patient P, as depicted in FIG. 4, from this contour and with optionally the movements of the patient being taken into account. Such a wire model G has nodes—depicted by the plotted solid black circles—at which the wire model is movable. The distances between the wire points in this case are embodied in a manner specific to the patient, i.e. adapted or registered or scaled to the proportions visible in the contour of the patient.

By means of appropriate statistical examinations of subjects with the aid of CT and/or MRI recordings, it is possible to determine mean or typical anatomical structures registered to the wire model. In this case, it is particularly advantageous if, additionally, standardizations or subdivisions according to sex, height, weight, etc. are also undertaken.

Figure 5:
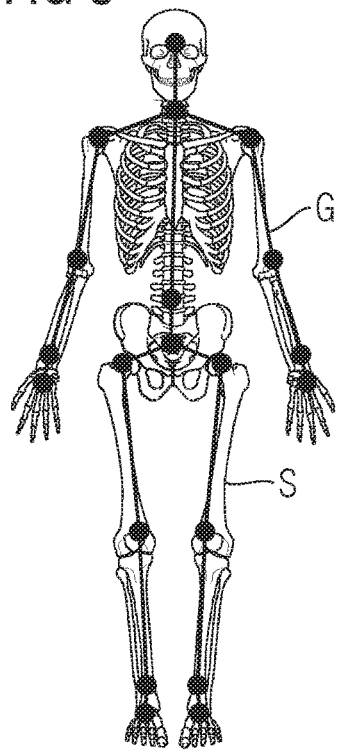
FIG. 5 is an illustration of a model of a skeleton registered on the wire model.
Figure 6:
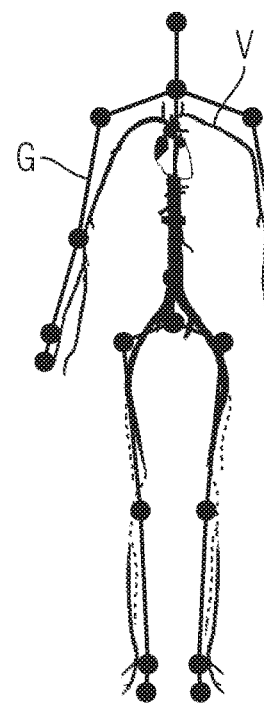
FIG. 6 is an illustration of a model of blood vessels registered on the wire model.
Figure 7:
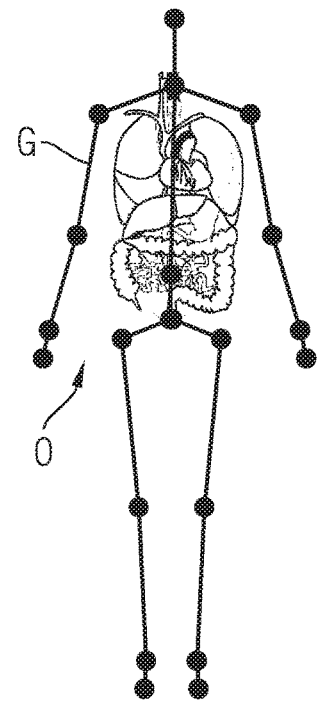
FIG. 7 is an illustration of an organ system registered on the wire model.

On the basis of the statistical material obtained thus, it is now possible to align and register the desired anatomical structure S, V or O on the basis of the wire model G. In FIGS. 5 to 7, an adapted skeleton S, an adapted venous and arterial system V and an adapted organ system O are depicted as anatomical structures in an exemplary manner.

According to the invention, the respective virtual anatomical structure S, V and O obtained thus is projected onto the patient situated on the patient couch, or it is shown on a monitor with the patient, for aligning x-ray tube and detector. As a result, the correct alignment of the recording system becomes substantially easier and it becomes permanently more precise.

Thus, overall, this invention shows an x-ray recording system, in which the contour of a patient is established with the aid of a TOF camera and, in a manner scaled to the contour, a wire model is generated in the form of a much-simplified skeleton with the essential joint and endpoints and the connections thereof. Representations of anatomical structures are then scaled to this wire model and depicted visually together with the patient. Thereupon, the operating staff is able to set the desired recording region for the x-ray recording in a very precise and accurate manner, supported by the visual representation of the anatomical structure together with the patient.

Even though the invention was illustrated more closely and described in detail by the preferred exemplary embodi- The following is a summary list of reference numerals and the corresponding structure used in the above description of the invention:
1 TOF camera
2 X-ray tube
2.1 Telescope and articulation system
3 X-ray detector/flat-panel detector
3.1 Telescope and articulation system
4 Rail system
6 Housing
7 C-arm
8 Patient couch
9 Computer unit
G Wire model
O Organ system
P Patient
S Skeleton/bony skeleton
V Venous and arterial system
Prg1-Prgn Software/programs

The invention claimed is:

1. An x-ray recording system, comprising:
an x-ray emitter for generating a beam used for imaging;
an imaging x-ray detector with a two-dimensional or three-dimensional recording geometry for determining an attenuation of rays of the beam;
a patient bearing and/or positioning device for a patient, in a recording region of the x-ray recording system between said x-ray emitter and said x-ray detector;
at least one time-of-flight (TOF) camera for establishing a contour of the patient;
a computer unit with a memory and software stored in said memory, said computer unit embodied, during operation, to generate a three-dimensional wire model of the patient with joint locations disposed therein from the contour of the patient recorded by said TOF camera and to simulate and display at least one virtual anatomical structure generated by statistical examination of the patient and scaled to the three-dimensional wire model; and
a projection system for projecting the at least one virtual anatomical structure onto the patient situated on said patient bearing and/or positioning device.

2. The x-ray recording system according to claim 1, wherein the at least one anatomical structure is a structure selected from the group consisting of a skeleton, a venous and/or arterial structure, and an organ structure.

3. The x-ray recording system according to claim 1, wherein said software stored in said computer unit is embodied to set a patient positioning in an automated manner in accordance with the at least one anatomical structure on a basis of a predetermined recording region by setting said patient bearing and/or positioning device and/or setting location and position of said x-ray emitter and/or said x-ray detector relative to one another and to the patient.

4. The x-ray recording system according to claim 1, further comprising:
a monitor; and
an optical camera for depicting the patient on said monitor, wherein the software stored in said computer unit is embodied to superpose, on said monitor, the at least one anatomical structure with a representation of the patient.

5. The x-ray recording system according to claim 1, wherein the software stored in said computer unit is embodied to display the recording region to be irradiated by the beam.

6. The x-ray recording system according to claim 1, wherein the software stored in said computer unit is embodied to automatically align a spatial position of said x-ray emitter in accordance with regions of the at least one anatomical structure to be recorded.

7. The x-ray recording system according to claim 6, further comprising a table or database specifying an ideal alignment of said x-ray emitter relative to a region of the anatomical structure.

8. The x-ray recording system according to claim 1, wherein said TOF camera is part of a KINECT or XTION acquisition system.

9. The x-ray recording system according to claim 1, wherein said TOF camera is disposed next to said x-ray emitter or next to said x-ray detector.

10. The x-ray recording system according to claim 1, wherein the x-ray recording system is configured as a C-arm system.

11. The x-ray recording system according to claim 1, wherein the x-ray recording system is embodied as a projective radiography system.

12. The x-ray recording system according to claim 11, further comprising articulated arms, said x-ray emitter and said x-ray detector are disposed on said articulated arms in a manner independent of one another and freely movable in space.

* * * * *